04-370 SP
/25/85 XR RE 31,922

United States Patent [19]

Mesek et al.

[11] E Patent Number: Re. 31,922

[45] Reissued Date of Patent: Jun. 25, 1985

[54] CONFORMABLE DISPOSABLE DIAPERS HAVING ABSORBENT PANEL WITH BULGED SIDE MEMBERS

[75] Inventors: Frederick K. Mesek; Virginia R. Mesek, both of San Diego, Calif.

[73] Assignee: Johnson & Johnson, New Brunswick, N.J.

[21] Appl. No.: 535,088

[22] Filed: Sep. 23, 1983

Related U.S. Patent Documents

Reissue of:

[64] Patent No.: 4,324,245
Issued: Apr. 13, 1982
Appl. No.: 106,182
Filed: Dec. 21, 1979

U.S. Applications:

[63] Continuation of Ser. No. 862,309, Dec. 20, 1977, abandoned.

[51] Int. Cl.[3] ..... A41B 13/02

[52] U.S. Cl. ..... 604/385 A; 604/370; 604/390

[58] Field of Search ..... 604/385

[56] References Cited

U.S. PATENT DOCUMENTS

| | | | |
|---|---|---|---|
| 109,410 | 11/1870 | Hughes . | |
| 2,119,610 | 6/1938 | Tasker | 128/284 |
| 2,273,542 | 2/1942 | Tasker | 128/284 |
| 2,419,867 | 4/1947 | Woodman | 2/224 |
| 2,468,445 | 4/1949 | Harst | 128/284 |
| 2,509,674 | 5/1950 | Cohen | 128/284 |
| 2,538,758 | 1/1951 | Bricmont | 128/287 |
| 2,627,859 | 2/1953 | Hargrave | 128/287 |
| 2,675,805 | 4/1954 | Trimble | 128/284 |
| 2,733,715 | 2/1956 | Folk | 128/284 |
| 2,866,459 | 12/1958 | Sobelson | 128/284 |
| 2,905,581 | 9/1959 | Maxey | 154/124 |
| 2,969,065 | 1/1961 | Farnsworth | 128/284 |
| 3,000,381 | 9/1961 | Mulhole | 128/284 |
| 3,407,813 | 10/1968 | Grippo | 128/287 |
| 3,417,751 | 12/1968 | Murdoch | 128/287 |
| 3,424,162 | 1/1969 | Parravicini | 128/288 |
| 3,461,872 | 8/1969 | McConnell | 128/287 |
| 3,488,778 | 1/1970 | Goujon et al. | 604/385 |
| 3,559,648 | 2/1971 | Mason | 128/287 |
| 3,658,064 | 4/1972 | Pociluyko | 128/287 |
| 3,744,494 | 7/1973 | Marsan | 128/287 |
| 3,776,232 | 12/1973 | Schaar | 128/287 |
| 3,776,233 | 12/1973 | Schaar | 128/287 |
| 3,807,402 | 4/1974 | Miller | 128/287 |
| 3,828,784 | 8/1974 | Zoephel | 128/287 |
| 3,860,003 | 1/1975 | Buell | 604/385 |
| 3,882,871 | 5/1975 | Taniguchi . | |
| 4,050,462 | 9/1977 | Woon et al. | 604/385 |

FOREIGN PATENT DOCUMENTS

| | | | |
|---|---|---|---|
| 1600732 | 9/1970 | France . | |
| 2063794 | 6/1971 | France . | |
| 2219636 | 9/1974 | France . | |
| 2251278 | 6/1975 | France . | |
| 2345955 | 10/1977 | France . | |
| 1164469 | 9/1969 | United Kingdom | 604/385 |

*Primary Examiner*—Stephen C. Pellegrino
*Assistant Examiner*—Sherri E. Vinyard
*Attorney, Agent, or Firm*—Martha A. Michaels

[57] ABSTRACT

A disposable diaper having constringent means in the longitudinal side margins is disclosed. The constringent means foreshortens the side margins and acts on an absorbent batt contained within the diaper to bulge the side margins of the batt.

34 Claims, 13 Drawing Figures

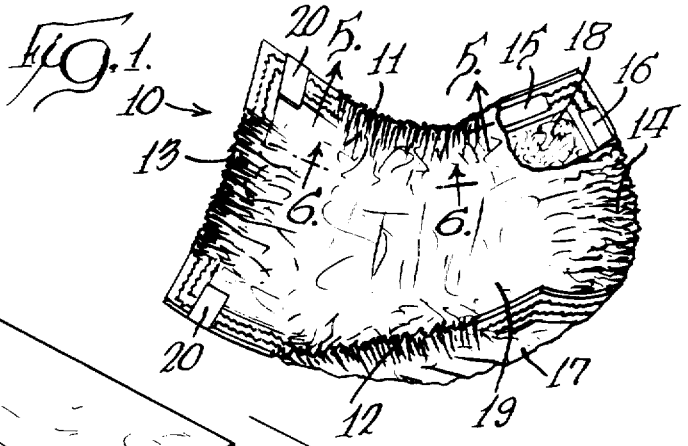
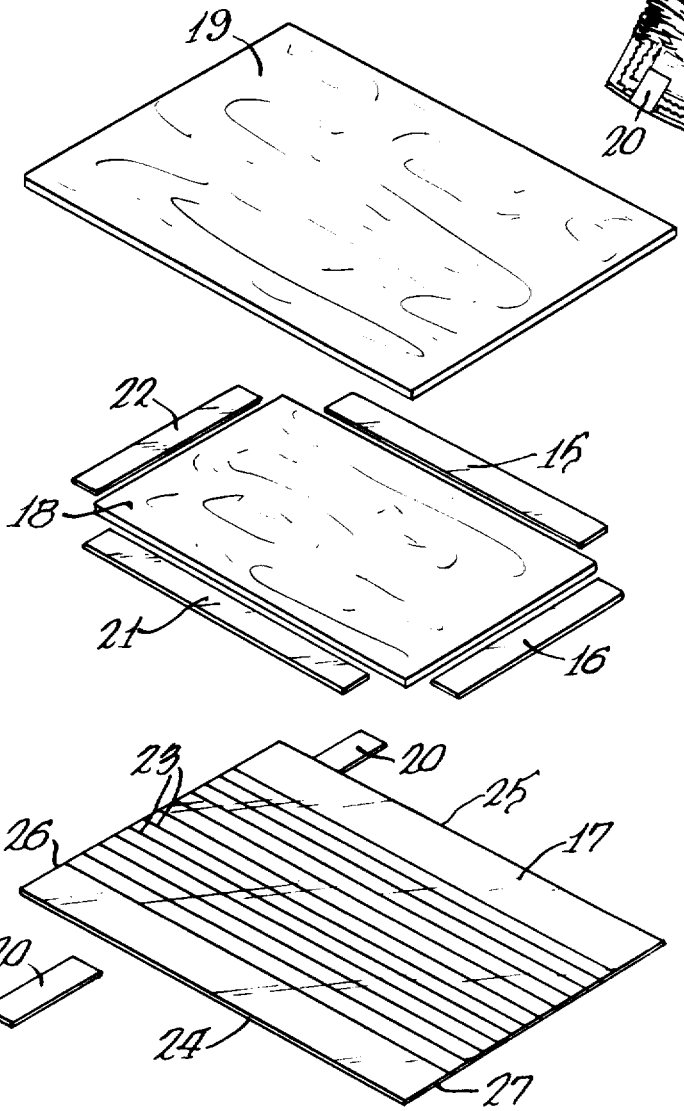
Fig. 2.
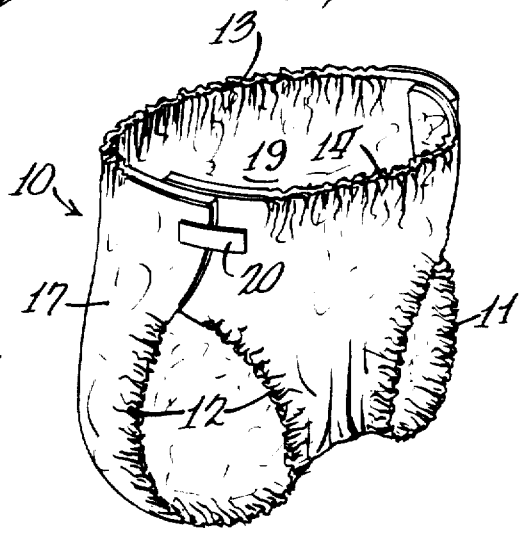
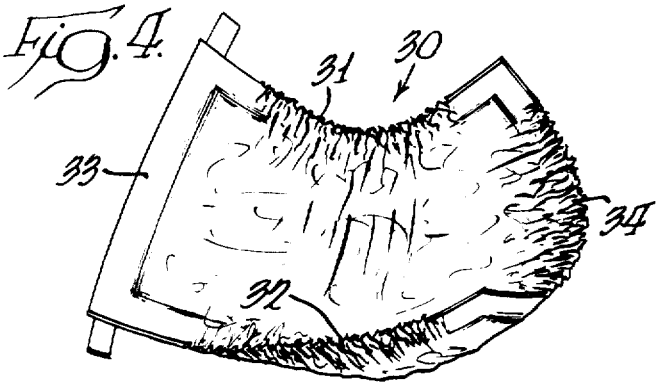

CONFORMABLE DISPOSABLE DIAPERS HAVING ABSORBENT PANEL WITH BULGED SIDE MEMBERS

Matter enclosed in heavy brackets [ ] appears in the original patent but forms no part of this reissue specification; matter printed in italics indicates the additions made by reissue.

This is a continuation of application Ser. No. 862,309, filed Dec. 20, 1977, and now abandoned.

BACKGROUND OF THE INVENTION

The present invention relates to improvements in disposable diapers which enable the diaper to closely conform to the torso of a baby, without sacrificing absorptive capacity. The diapers of the present invention accomplish this without causing any discomfort to the baby, while at the same time providing improved gasketing around the thighs and resultant fluid containment.

In the recent past disposable diapers have been introduced into the market place which have a narrow but relatively thick strip of elastic at each side thereof, so as to gather the side margins of the diaper in a manner similar to that of conventional moisture-impermeable panties. Such diapers are made generally in accordance with the teachings of U.S. Pat. No. 3,860,003. In order for the elastic members to be effective in such diapers, it is necessary that the elastic members be spaced relatively far from the side marginal edges of the absorbent panel of the diaper, and for the elastic members to be associated with thin, highly flexible facing and backing layers. As a result, when such diapers are placed upon a baby, the narrow but relatively thick elastic members cause a narrow band of the facing layer to bear against the baby's skin with substantially line contact. This results in a high degree of stress concentration that may cause pinching and irritation of the baby's skin.

The problems attributable to the unduly high compressive force caused by such narrow but relatively thick elastic strips of the prior art diapers mentioned above are particularly acute when the baby has voided and the diaper is wet. Because the backing and facing layers are so highly flexible, when the diaper is wet and conditions are present tending to cause hydration of the baby's skin, the narrow elastic members [often] *sometims* cause the facing layer to press against the skin with sufficient force to injure the skin. Also, the elastic members in prior art diapers of the type described above cause the diaper to gradually creep upwardly upon the baby's thighs. As a result, the forces applied to the skin by the stressed elastic members increase the longer the diaper is worn.

One of the most serious drawbacks with prior art diapers of the above mentioned type is that in order to give the diaper sufficient flexibility at the sides to permit gathering, the absorbent panel has been narrowed in the midportion, or lightened to such an extent that the absorbent capacity of the diaper *in the critical area* is significantly reduced.

While many attempts have been made in the past to provide diapers, both disposable and non-disposable, with improved fit characteristics without sacrificing absorptive capacity, heretofore such efforts have not met with success.

SUMMARY OF THE INVENTION

In addition to those elements which are present in currently commercially available products, i.e., a moisture pervious facing adapted to engage the baby's skin, an absorbent batt or panel adjacent to the facing, and an outer moisture impervious backing over the absorbent batt, the diapers of the present invention include constringent means at each side of the diaper which are effective to not only gather the longitudinal margins of the diaper, but also to [foreshorten] *reduce the length of the side margins of* the absorbent panel and create pillow-like marginal bulges therein. In the preferred embodiment, the constringent means is provided by relatively wide but thin elastic members that are secured to the backing *and/or facing* and are located sufficiently closely to the side margins of the absorbent panel so that constringing forces generated by the elastic members are transmitted to the *sides of the* absorbent panel at least through the backing, thereby causing at least the sides of the absorbent panel to buckle and/or bulge. By the term "relatively wide," the present invention contemplates that elastic members have a width of at least $\frac{1}{4}''$, *preferably a width of at least* $\frac{1}{2}''$, and *more* preferably a width from about $\frac{3}{4}''$ to about $1\frac{1}{4}''$. The width-to-thickness ratio of the preferred constringent means is at least about 100.

*It is contemplated that the relatively wide elastic members may be provided by two or more relatively narrow* ($\frac{1}{4}''$ *or less*) *elastic members that are positioned in spaced parallel relationship with respect to one another, and which cooperate to function as though they are essentially one elastic member having a width dimension that is measured between the outer edges of the outer elastic members. And, it is also contemplated that the relatively wide elastic members may be provided by round, or flattened elastic tubes, woven bands, reticulated bands, or elastic monofilaments that are arranged to provide the desired force distribution.*

Diapers constructed in accordance with the present invention have several unexpected advantages, particularly as compared to the prior art diapers of the type disclosed in U.S. Pat. No. 3,860,003. In this regard, by utilizing relatively wide elastic members as the constringent means, the area of the facing that is pressed against the baby's skin is relatively large so as to distribute the force applied to the skin over a relatively large area and to minimize the possibility of irritation. Because of the relatively large area of facing engaging the baby's skin *and the bulged side margins of the panel*, improved gasketing around the thighs is effected, thereby minimizing leakage from the diaper. In this regard, it is significant that absorptive materials effect at least in part the gasketing action, in contradistinction to the relatively non-absorbent facing in U.S. Pat. No. 3,860,003 which provides little, if any, gasketing action. [Furthermore, the relatively wide band of engagement on the baby's thighs provides adequate friction for preventing relative movement between the baby's thigh and the diaper as the baby moves about.]

[A further benefit derived from the use of relatively wide but thin elastic members is that they are much easier to control and apply in a high speed manufacturing operation than narrow elastic members.]

As will appear in more detail from the following description, diapers of the present invention provide improved fit, and improved gasketing (or sealing) around the baby's legs, without loss of absorptive capacity and without irritation to the baby's skin.

BRIEF DESCRIPTION OF THE DRAWINGS

In the drawings,

FIG. 1 is a perspective view illustrating a disposable diaper embodying the present invention with a portion broken away to show interior detail;

FIG. 2 is an exploded perspective view showing relative positioning of diaper elements during manufacture of the diaper depicted in FIG. 1;

FIG. 3 is a perspective view of the diaper of FIG. 1 illustrating diaper configuration when applied about a baby;

FIG. 4 is a perspective view showing another embodiment of the disposable diaper of this invention;

DESCRIPTION OF THE PREFERRED EMBODIMENTS

Figure 5:
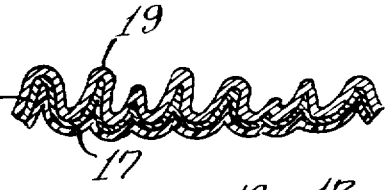
FIG. 5 is a sectional view, on an enlarged scale, taken along plane 5—5 in FIG. 1.

For a disposable diaper of the present invention the constringent means is a readily stretchable, elastic, *preferably* thermoplastic member of substantial width that possesses a certain minimum elastic recovery.

The term "elastic," as used herein, refers to sheets, films, ribbons and the like which have a recovery of at least *90* percent, when elongated [at least below their elastic limit and measured in accordance with the following formula:

$$\text{Percent retraction} = (L_e - L_t)/(L_e - L_o)$$

] *to within 10 percent of their yield point and measured in accordance with the following formula:*

$$\textit{Percent retraction} = (L_e - L_t)/(L_e - L_o) \times 100$$

where $L_o$ = original length of sample $L_e$ = fully extended length $L_t$ = length of sample measured *3* seconds after released from extended length.

The thickness of the elastic member generally is 10 mils or less, and preferably about 0.5 to about 5 mils. The elastic member has [an extensibility to rupture of at least about 300 percent, preferably about 400 to about 1000 percent and a recovery of 50 percent elongation of at least about 75 percent, and preferably at least about 80 percent. For ease of stretchability, the modulus of elasticity of the elastic member at 50 percent elongation should not exceed about 2000 pounds per square inch, and preferably is about 100 to about 200 pounds per square inch] *a recovery at 50 percent elongation after 3 seconds and preferably instantaneously of at least about 90 percent, and preferably close to 100 percent. For ease of stretchability, the modulus of elasticity of the elastic member at 50 percent elongation should not exceed about 2000 pounds per square inch. The modulus of elasticity is preferably substantially less than 2000 pounds per square inch, and most preferably is about 20 to about 200 pounds per square inch* .

It is important that the elastic members in the longitudinal side margins of the diaper not only [foreshorten, i.e.] *shorten, e.g.*, gather, the side margins but also act on the adjacent sides of the absorbent batt to create pillow-like bulges or convolutions that shape the absorbent batt in the perineal region of the infant for comfort and gasketing but without incurring a penalty with respect to absorbent capacity. The elastic members can act directly on the *sides of the* absorbent batt when in physical contact therewith, or can act through the backing and/or the facing. In any event, the recovery force of an extended elastic member must be sufficient to overcome the resistance to deformation offered by the relatively stiff absorbent batt. *And, the relationship between the elastic members and the batt is such that while the elastic members are effective to bulge the sides of the batt, the central region of the batt is not compacted or gathered which would result in the presence of too much bulky material between the legs of the infant and detract from the fit of the diaper.* Preferably, the elastic member extends laterally substantially across the entire width of the diaper side margin; however, in instances where the tensile modulus of the elastic member is relatively high, the elastic member can be spaced from the absorbent batt.

Any gathering of the diaper side margins that takes place because of the relaxation of elastic bands present in the diaper side margins necessarily increases the thickness dimension of the margins, thereby making effective gasketing difficult, and usually requires an excessive compressive force on the baby's thighs. The diaper construction of the present invention, on the other hand, by providing relatively wide but thin elastic members in the diaper side margins provides effective gathering not only of the side margins but also longitudinal constringement of the adjacent batt *side* margins without an attendant undesirable increase in side margin thickness.

In the preferred embodiment of the present invention the constringent means have a width of at least about $\frac{1}{4}$", *preferably a width of at least* $\frac{1}{2}$", and more preferably *a width of from* about $\frac{3}{4}$" to about $1\frac{1}{4}$". The width-to-thickness ratio should be at least about 100 and preferably about 500 to about 1000.

Referring to FIG. 1, disposable diaper 10 embodying the present invention is provided with marginal longitudinal constringent means in opposite side margins 11 and 12 adapted to provide enhanced fit and gasketing about the baby's thighs. Additionally, optional transverse constringent means are provided in end margins 13 and 14 for enhanced fit about the baby's waist. The constringent means in each of the side margins is a relatively wide but thin elastic member, such as elastic member 15 in side margin 11. The optional transverse constringent means in the end margins of diaper 10 can be a similar elastic member each as member 16 in end margin 14. Diaper 10 additionally includes first outer layer or backing 17 made of a moisture-impervious web, a generally rectangular absorbent batt 18 positioned in superposed relationship with respect to the backing, and second outer layer or facing 19 made of a moisture-pervious web and positioned in superposed relationship with respect to absorbent batt 18. For securement about a baby, diaper 10 is provided with pressure-sensitive adhesive tape tabs 20 and 21. The longitudinal constringent means are generally parallel to the longitudinal side margins of batt 18, and when the constringent means are in a relaxed state, diaper 10 assumes a boatlike configuration as shown in FIG. 1 with side margins 11 and 12 [foreshortened] *having a reduced length* . As will be discussed in greater detail hereinbelow, the constringent means also act on the respective adjacent side margins of absorbent batt 18 and longitudinally constringe the side margins of batt 18 creating pillow-like marginal bulges or convolutions therein.

The individual components of disposable diaper 10 are illustrated in FIG. 2. Absorbent batt 18 is superposed over backing 17 and is secured thereto by a series of glue lines 23 deposited on backing 17. Absorbent batt 18 is of smaller area than backing 17 and, when substantially centered on backing 17, is spaced from longitudinal sides 24 and 25 as well as transverse sides or ends 26 and 27 and thereby defines the side and end margins of diaper 10. Absorbent batt 18 is flanked on all four sides thereof by elastic film members 15, 16, 21 and 22 which, in an extended state, are secured to backing 17 by means of an elastic adhesive, sonic sealing, or in any other convenient manner. Moisture-pervious facing 19 is superposed over absorbent batt 18, is larger in area than batt 18, and is secured to backing 17, usually by means of the exposed end portions of glue lines 23. However, other securement means can be utilized, if desired. Facing 19 is also secured to elastic film members 15, 16, 21 and 22 in a manner similar to the securement thereof to backing 17.

*Batt 18 preferably is provided with a densified skin in accordance with the teachings of commonly assigned U.S. Pat. No. 3,938,522 to Repke, the disclosure of which is hereby incorporated herein in its entirety by this reference. Glue lines 23 penetrate the densified skin and cooperate with it to stiffen the mid-portion of the batt and prevent the central portion of the diaper from buckling or gathering under the influence of the constringent means hereinafter described.*

Figure 6:
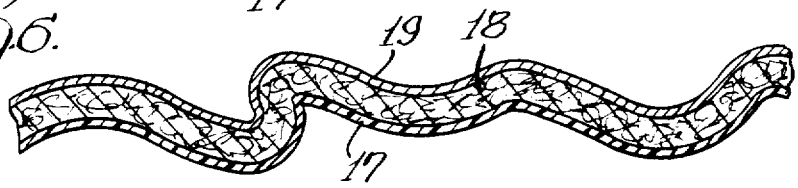
FIG. 6 is a sectional view, on an enlarged scale, taken along plane 6—6 in FIG. 1.

The action of a relaxed constringent means on the rest of diaper components is illustrated in FIGS. 5 and 6. The direct action of elastic member 15 on facing 19 and backing 17 secured thereto gathers the resulting laminar composite forming a plurality of gathers or macropleats (FIG. 5) in side margin 11. At the same time elastic member 15 acts on the adjacent side margin of absorbent batt 18 to produce controlled pillow-like convolutions or bulges (FIG. 6) *at the sides thereof. Because of the aforementioned cooperative action of the densified skin and the glue lines, the central portion of the batt, and the central portion of the other diaper components, are not influenced by the constringent means, and hence remain ungathered. Thus, in accordance with the present invention there is a transition from gathers at opposite side margins of the diaper, to bulges inwardly of the side margins and generally in alignment with opposite sides of the batt, and finally to a relatively smooth and undisturbed diaper mid-portion. The generally smooth mid-portion of the batt occupies at least 20 percent of the batt width dimension and preferably from about 50 percent to about 80 percent. The bulges in the side margins of the batt have a maximum height dimension at the sides of the batt, and taper generally uniformly inwardly to the generally smooth batt mid-portion.*

The configuration that disposable diaper 10 assumes when applied to a baby is illustrated in FIG. 3. Partially-extended diaper side margins 11 and 12 provide a comfortable yet positive seal about the baby's thighs that readily accommodates leg movements of the baby, while optional elastic members in diaper end margins 13 and 14 assure good fit about the baby's waist.

FIG. 4 shows disposable diaper 30 that is similar to disposable diaper 10 but lacks the optional elastic member in diaper end margin 33. In the embodiment exemplified by FIG. 4 the elastic member in diaper end margin 34 is similar to elastic member 16 in FIG. 1 and performs in the same manner. The construction of diaper side margins 31 and 32 is substantially the same as in diaper side margins 11 and 12.

Figure 7:
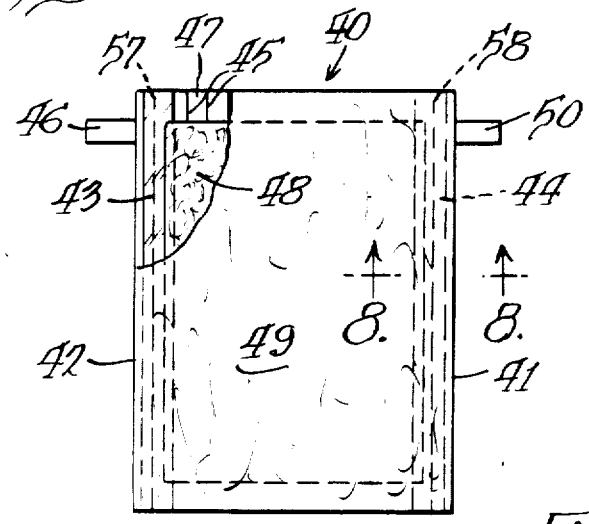
FIG. 7 is a plan view of a further embodiment of a disposable diaper of this invention with a portion broken away to show interior detail.
Figure 8:
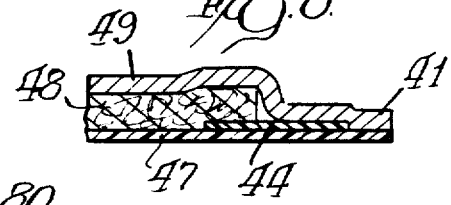
FIG. 8 is a sectional view, on an enlarged scale, taken along plane 8—8 in FIG. 7.

Another embodiment within the purview of the present invention is illustrated in FIGS. 7 and 8. In disposable diaper 40, elongated thin elastic ribbons 43 and 44 are secured to diaper backing 47 and diaper facing 49 so that a portion of each of ribbons 43 and 44 underlies substantially rectangular absorbent batt 48 and provides direct constringent action on the side margins of batt 48 when relaxed to [foreshorten] *reduce the length of* diaper side margins 41 and 42. If necessary, side margins of absorbent batt 48 can be secured, by means of an adhesive or in any other convenient manner, to respective underlying portions of elastic ribbons 43 and 44; however, usually it is not necessary to do so inasmuch as the coefficient of friction between the resulting contiguous surfaces is sufficient to transmit a constringing force from elastic ribbons 43 and 44 to batt 48. Usually absorbent batt 48 overlies less than about one-half of the width of the elastic ribbons 43 and 44. Central glue lines 45 provide attachment means for absorbent batt 48 and facing 49 to backing 47. Outer glue lines 57 and 58 provide further securement of respective elastic ribbons 43 and 44 to backing 47. Adhesive tape tabs 46 and 50 provide diaper securement means when diaper 40 is applied about a baby.

Figure 9:
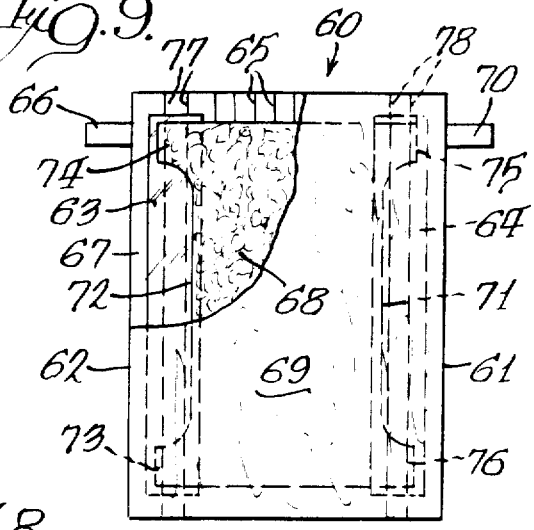
FIG. 9 is a plan view of yet another embodiment of a disposable diaper of this invention with a portion broken away to show interior detail.

In the embodiment illustrated by FIG. 9, disposable diaper 60 is provided with absorbent batt 68 having curvilinear side cut-outs 71 and 72 and sandwiched between facing 69 and backing 67. Glue lines 65 serve to secure batt 68 and facing 69 to backing 67. Relatively wide elastic ribbons 63 and 64 are situated in generally rectilinear diaper side margins 62 and 61, respectively, so that an innermost central portion of each of elastic ribbons 63 and 64 underlies adjacent side margins of absorbent batt 68. Elastic ribbons 63 and 64 extend substantially the entire length of diaper side margins 62 and 61, respectively, and are intermittently secured both to backing 67 and facing 69 so as to provide the desired gathering. In addition, paired outer glue lines 77 and 78 provide further securement of elastic ribbons 63 and 64 to backing 67. Protruding ears 73, 74, 75 and 76 of absorbent batt 68 overlap substantially the entire width of the respective elastic ribbons 63 and 64 and provide additional absorbent capacity which can be readily utilized by building into absorbent batt 68 appropriate capillary transport means. Adhesive tape tab means 66 and 70 provide means for securing diaper 60 about a baby.

Figure 10:
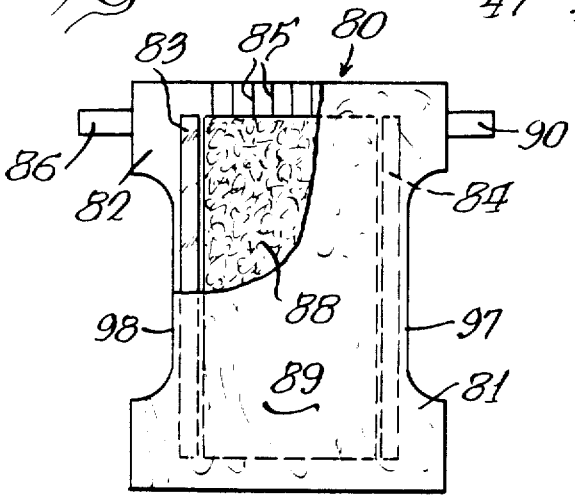
FIG. 10 is a plan view of a still further embodiment of a disposable diaper of this invention with a portion broken away to show interior detail; [and]

In the embodiment of FIG. 10, disposable diaper 80 is provided with substantially rectangular absorbent batt or panel 88 having generally rectilinear sides, sandwiched between backing 87 and facing 89, and together with backing 87 and facing 89 defining diaper side margins 81 and 82. Curvilinear cut-outs 97 and 98 are provided in the respective central portions of margins 81 annd 82 for further fit enhancement. Pre-stretched elastic film ribbons 83 and 84 are positioned in respective margins 82 and 81 and are secured to backing 87 and facing 89 along the longitudinal sides of absorbent panel 88. Glue lines 85 secure facing 89 and absorbent panel 88 to backing 87, and adhesive tape tabs 86 and 90 provide diaper securement means.

Figure 11:
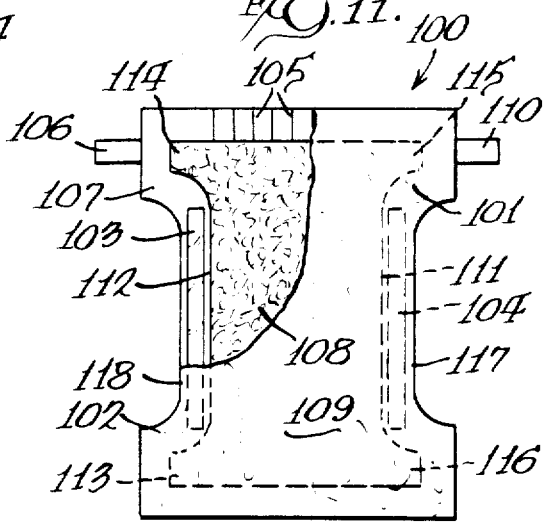
FIG. 11 is a plan view of an additional embodiment of a disposable diaper of this invention with a portion broken away to show interior detail.

Yet another embodiment of a disposable diaper according to the present invention is shown in FIG. 11 where disposable diaper 100 is provided with shaped absorbent panel 108 having curvilinear cut-outs 111 and 112 and centrally juxtaposed between backing 107 and facing 109. Both panel 108 and facing 109 are secured to backing 107 by a plurality of longitudinally extending glue lines 105. Curvilinear cut-outs 117 and 118, similar in configuration but of smaller size than cut-outs 111 and 112, are provided in the side portions of facing 109 and backing 107 that form diaper side margins 101 and 102, respectively, so that margin cut-out 117 subtends panel cut-out 111 and margin cut-out 118 subtends panel cut-out 112. Elastic film member 103 is positioned in diaper margin 102 between protruding ears 113 and 114 of absorbent panel 108 and is intermittently secured to facing 109 and backing 107 in a prestretched state at an elongation of at least about 50 percent and preferably about 100 percent. In a similar manner, elastic film member 104 is positioned in diaper margin 101 between protruding ears 115 and 116 of absorbent panel 108 and is secured to facing 109 and backing 107. Diaper securement means are provided by adhesive tape tabs 106 and 110.

Figure 12:
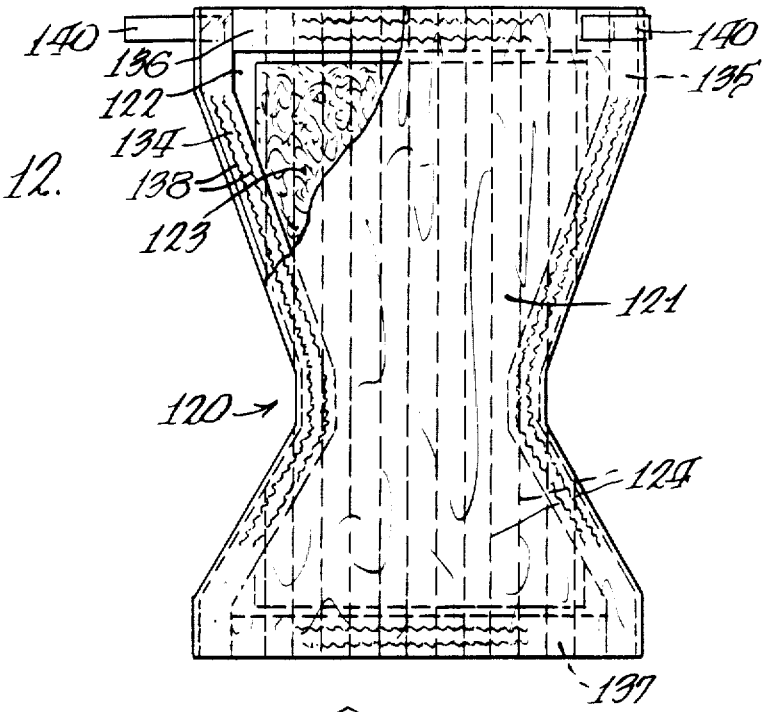
*FIG. 12 is a plan view of still another embodiment of a disposable diaper of this invention with a portion broken away to show interior detail; and*
Figure 13:
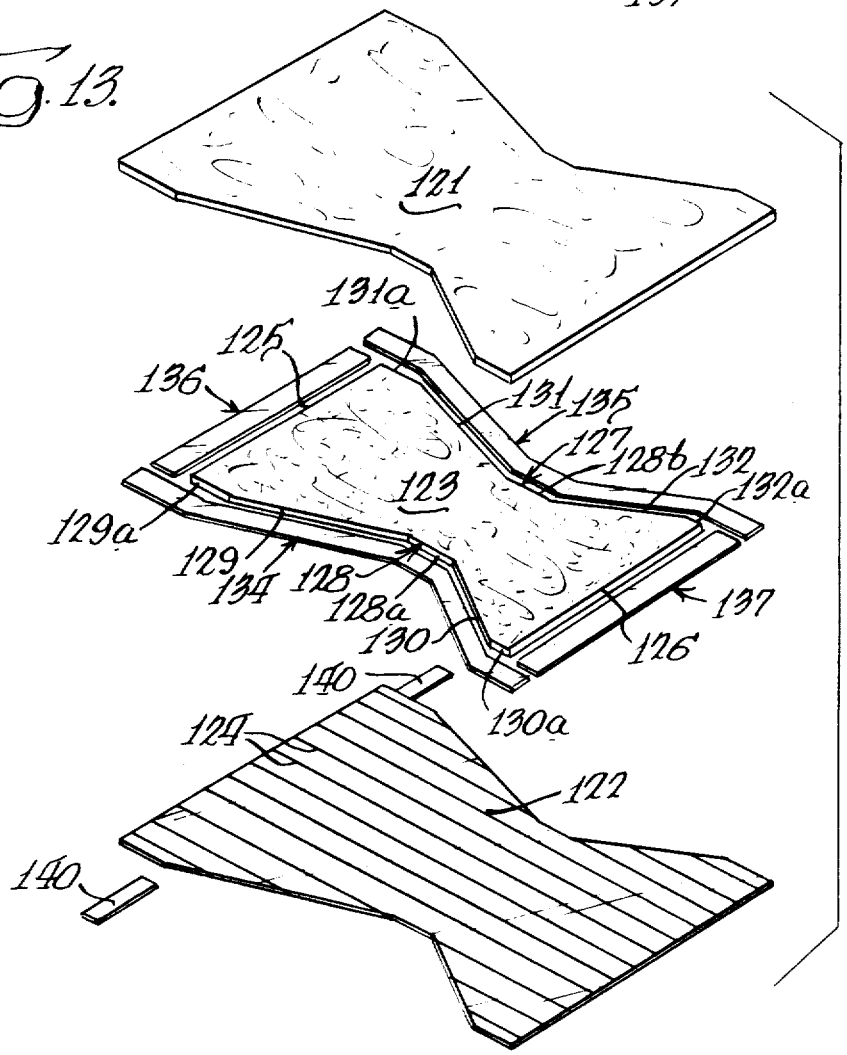
*FIG. 13 is an exploded perspective view showing relative positioning of diaper elements during manufacture of the diaper illustrated in FIG. 12.*

*Referring now to FIGS. 12 and 13, a still further embodiment of the invention is illustrated in its entirety at 120, and includes a first outer layer 121 in the form of a moisture pervious facing, a second outer layer 122 in the form of a moisture impervious backing, and a third layer 123 in the form of an absorbent batt sandwiched therebetween. Outer layers 121 and 122 have the same outer dimensions and are coterminous with one another. Batt 123 has an external configuration similar to layers 121 and 122, and is smaller than and centered relative to layers 121 and 122. Parallel glue lines 124 on backing 122 secure the batt to the backing, and the outermost glue lines (and the ends of the intermediate glue lines) secure the portions of layers 121 and 122 that extend beyond batt 123 to one another.*

*The end portions 125 and 126 of batt 123 are generally equal in width and are wider than the batt mid-portion 127. For improved fit, the narrowest part 128 of the batt mid-portion is offset toward batt end portion 126, the portion that is adapted to be placed in front of the infant. Batt portion 128 is of relatively short length and is formed between parallel side edges 128a and 128b. Batt side edges 129, 130, 131 and 132 flare outwardly from the ends of edges 128a and 128b and terminate in end portion 129a parallel with end portion 131a and end portion 130a parallel with end portion 132a. In a most preferred embodiment of the invention, edges 129 and 131 are disposed at an angle of 25° and edges 130 and 132 are disposed at an angle of 35°, so that the included angle between edges 129 and 130 and edges 131 and 132 is 120°.*

*As with the previously described embodiments, diaper 120 includes constringent means 134 and 135 at opposite sides of the diaper, and optional constringent means 136 and 137 at opposite ends of the diaper. The illustrated constringent means are in the form of elongated elastic members that are secured in a stretched condition to layers 121 and/or 122. The securement means may take the form of one or more spaced rows 138 of spaced securement zones. The elastic members which form the constringent means 134 and 135 are parallel with the side edges of the batt between the overlapping side edges of layers 121 and 122 for improved application of constringing forces to not only the side margins of the facing and backing layers, but also the sides of the panel 123. The elastic members extend beyond the ends of the panel 123, and completely from end to end of the diaper.*

*As with the previously described embodiments, tape tabs 140 are provided for securement of the diaper about an infant.*

Elastic film members suitable as constringing elements for the diapers contemplated herein can be extruded to the desired thickness utilizing unvulcanized, thermoplastic compositions which are made up of an elastomeric component and an optional compatible modifier which is a thermoplastic polymer of a relativley low molecular weight but solid at ambient temperature.

Illustrative of the elastomeric components suitable for present purposes are block copolymers which comprise terminal thermoplastic polymer blocks and at least one non-terminal or intermediate elastomeric polymer block. Block copolymers of this general type may be prepared using a step-wise polymerization initiator, e.g., an organolithium compound. Such block polymerization techniques are well known in the art.

The elastomeric component can be linear or radial $A^1$-B-$A^2$ block copolymers or mixtures thereof with simple $A^1$-B block copolymers where $A^1$ and $A^2$ can be alike or different and represent a thermoplastic polymer block, such as poly(vinyl arene) block, and B represents an elastomeric polymer block such as a conjugated diene or a lower (i.e., $C_1$-$C_4$) alkene. The modifier component is a low molecular weight thermoplastic polymer having an average molecular weight of about 500 to about 7,500 and is present in the composition in an amount of about zero to about 200 parts by weight per 100 parts by weight of the elastomeric component.

A preferred thermoplastic film composition for the elastic film members comprises an elastomeric component which contains, as a major constituent thereof, an unvulcanized linear block copolymer of the general configuration $$A^1\text{-}B\text{-}A^2$$

wherein $A^1$, $A^2$ and B have the same meaning as hereinabove. In these block copolymers the A-blocks are derived from styrene or sytrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to about 200 parts by weight per 100 parts by weight of the elastomeric component.

The preferred $A^1$-B-$A^2$ block copolymers have A-blocks derived, i.e., polymerized or copolymerized, from styrene or styrene homologues; and B-blocks derived from conjugated dienes, such as isoprene or butadiene, or from lower alkenes, such as ethylene and butylene. Small proportions of other monomers also may enter into the block copolymers themselves. The individual A-blocks can have an average molecular weight of at least about 6000, preferably in the range of about 8000–30,000, and the A-blocks constitute about 5–50 percent, preferably about 10–30 percent, by weight of the block copolymer. The average molecular weight of the B-blocks for linear $A^1$-B-$A^2$ block copolymers preferably is in the range of about 45,000–18,000 and that of the linear copolymer, itself, preferably is in the range of about 75,000–200,000. The average molecular weight of the radial $A^1$-B-$A^2$ block copolymers preferably is in the range of about 125,000–400,000. The term "linear block copolymer" (or copolymers) includes branched $A^1$-B-$A^2$ copolymers as well as unbranched $A^1$-B-$A^2$ copolymers.

The radial $A^1$-B-$A^2$ copolymers useful for manufacture of elastic members for diapers of this invention are of the type described in U.S. Pat. No. 3,281,383 to Zelinski et al. and conform to the following general formula: $(A\text{-}B\text{-})_nX$, wherein A is a thermoplastic block polymerized from styrene or styrene homologues, B is an elastomeric block derived from conjugated dienes or lower alkenes, as indicated above, X is an organic or inorganic connecting molecule, with a functionality of about 2 to 4 as described in U.S. Pat. No. 3,281,383, or possibly with a higher functionality as described in the article entitled "New Rubber is Backed by Stars" appearing on page 35 of the June 11, 1975 issue of Chemical Week. As used hereinabove, "n" has a value corresponding to the functionality of X.

The preferred elastic film member is highly thermoplastic and, though elastomeric, is unlike rubber in that the film exhibits a relatively sharp melting point and is capable of being heat shaped. Also, the elastic film member can form permanent heat seals to substrates such as non-woven fabrics, or the like, at relatively low heat sealing peak temperatures, generally not above about 350° F. The film member is highly elastic and has a relatively low rubber modulus, i.e., it exhibits in at least one direction an elastic recovery, from 50 percent stretch to at least 75 percent, preferably at least about 80 percent, and a 50 percent rubber modulus of not above about 2000 pounds per square inch, preferably [not above 1000 pounds] *in the range of about 20 to about 200 pounds* per square inch at 50 percent elongation. The film member also is very flexible, extensible and soft and normally exhibits a Gurley stiffness of about one or less at a film thickness of one mil, and an elongation to break of at least about 300 percent, preferably at least about 400 percent, in at least one direction at ambient temperatures.

*While the constringent means described above is in the form of a single elastic ribbon at opposite sides of the diaper, the present invention is not limited thereto, and it is contemplated that other forms of constringent means may be provided, so long as the constringent means is effective to bulge the side margins of the batt. In this regard, it is contemplated that each side margin of the diaper may include a plurality of spaced, parallel longitudinally extending elastic members; such as, bands, round or flattened tubes, monofilaments, etc.*

*By way of example, and with reference to FIG. 1, the illustrated ribbons 15 and 21 may be replaced by a pair of ¼" wide elastic bands that are parallel with one another and with the adjacent side edge of the batt. With such an arrangement, the innermost elastic bands would be disposed directly adjacent to the side edge of the batt, and the center lines of the bands would be spaced from one another by ¾". It will be recognized that such a constringent means is less costly than a construction that uses a 1" wide elastic member, because less material is utilized Nevertheless, it is possible to effect the desired gathering at the sides of the diaper, and bulging of the side margins of the batt, without undue stress concentration upon an infants skin, since the pulling force of the plural elastic members is distributed over a relatively large area. Stated differently, the desired results of the invention can be achieved by the use of plural elastic members at each side of the diaper, since the pulling force required for each elastic member is less than that required for a single elastic member and the amount of pre-stretch for the individual plural elastic members can be reduced accordingly, With such an arrangement it is also possible to pre-stretch the elastic members a different amount, if desired or necessary, to achieve the desired panel bulging effect.*

Several different types of facing materials may be used for diaper facing. For example, the facing may be a non-woven web made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,633,348 to Liloia et al.

Non-woven facing materials suitable for use in disposable diapers of this invention can have fabric weights in the range of about [1] *0.5* to 5 oz./yd.$^2$ and densities of less than 0.15 g./cc., generally in the range of about 0.05 to about 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics.

Facing may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a fibrous polyester type material can have a weight of about 0.75 oz./yd.$^2$.

*The facing may be the same size as, and coterminous with, the backing; or alternatively, the facing may be wider than the backing and have its side edges inwardly folded so that the facing is coterminous with the backing, as is shown in FIG. 3 of U.S. Pat. No. 3,612,055. In the latter case, the*

*elastic members may be secured above the inwardly folded side edges of the facing.*

In addition, facings can be formed of a non-apertured material, such as a non-woven isotropic web, or of an apertured polyolefin or polyester film having the desired moisture permeability. In all of the aforementioned facings the material should be relatively hydrophobic so as to retard wicking within the facing.

The moisture-absorbent batt or panel of a desired shape but smaller than the facing and the backing, can be formed in accordance with the teachings of U.S. Pat. No. 3,612,055 to Mesek et al.

A suitable backing material for the diapers embodying the present invention can be an opaque polyolefin, e.g., polyethylene, web about 0.001 inch thick. Another suitable material for this purpose is a polyethylene terephthalate web having a thickness of about 0.0005 inch.

In use, the disposable diaper is applied to the baby by laying out the diaper on a suitable flat surface and placing the baby thereon so that the waist-underlying end of the diaper is that having the fastener means. The other end of the diaper then extends downwardly between the infant's legs. Next, the downwardly extending end of the diaper is brought up between the baby's legs to a position covering the perineum and contiguous with the front portion of the baby's waist. The diaper is thereafter secured to the baby by placing the corners of the waist portion of the abdomen-covering end as far around the baby's waist as they will go and by bringing the corners of the underlying end of the diaper into an overlapping relationship with the aforementioned corners so that the diaper snugly encircles the baby's waist and provides a custom fit. The adhesive tab fasteners are then prepared for use and the diaper is secured in the desired position by simply urging the pressure-sensitive adhesive surface of the tape tab in contact with the adjacent outer surface of the opposite corner of the diaper. The applied diaper assumes a configuration such as shown in FIG. 3.

The foregoing description and the drawings are illustrative and are not to be taken as limiting. Still other variations and modifications are possible without departing from the spirit and scope of the present invention.

I claim:

1. A disposable diaper comprising: a first outer layer in the form of a moisture impervious backing; an absorbent batt positioned in superposed relationship with respect to said backing, said batt being smaller than said backing and spaced inwardly from the sides and ends thereof; a second outer layer in the form of a moisture pervious facing positioned in superposed relationship with respect to said batt, said facing being larger than said batt and having marginal portions thereof secured to said backing; constringent means in each side margin of the diaper for foreshortening the side margins of the diaper; said constringent means cooperating with said outer layers and said batt to bulge the side margins of the batt, in addition to gathering the side margins of the outer layers adjacent thereto, the central portion of said outer layers and said batt being generally smooth and ungathered.

2. The disposable diaper in accordance with claim 1 wherein said constringent means is an elastic ribbon at least about one-half inch wide and having a width-to-thickness ratio of at least about 100.

3. The disposable diaper in accordance with claim 1 wherein said constringent means is an elastic ribbon of thermoplastic material intermittently heat sealed in place.

4. The disposable diaper in accordance with claim 1 wherein a transverse constringent means is provided in at least one end margin of the diaper.

5. The disposable diaper in accordance with claim 1 wherein a transverse constringent means is provided in both end margins of the diaper.

6. The disposable diaper in accordance with claim 1 wherein said constringent means is an elastic ribbon, and wherein a portion of said elastic ribbon underlies said absorbent batt.

7. The disposable diaper in accordance with claim 1 wherein said absorbent batt is rectangularly shaped, said constringent means each being parallel to one side edge of the absorbent batt.

8. The disposable diaper in accordance with claim 7 wherein said first and second outer layers are rectangular and generally coterminous with one another.

9. The disposable diaper in accordance with claim 7 wherein said first and second outer layers are hour-glass shaped and generally coterminous with one another.

10. The disposable diaper in accordance with claim 1 wherein a recess is provided at each side of the batt to form outwardly extending ears at each batt corner, said constringent means being located within said recess.

11. A disposable diaper comprising: a first outer web in the form of a moisture impervious backing; an absorbent batt positioned in superposed relationship with respect to said backing, said batt being smaller than said backing, being spaced inwardly from the sides and ends thereof, and defining sides and end margins of the diaper, respectively; a second outer web in the form of a moisture pervious facing positioned in superposed relationship with respect to said batt, said facing being larger than said batt and having marginal portions thereof secured to said backing; an elastic member positioned along each side margin of the diaper; means securing each said positioned elastic member to at least one of said outer webs in a condition where the elastic member, when in a relaxed state, is effective to foreshorten at least a portion of the diaper side margin with which the elastic member is associated; each elastic member extending substantially across the entire width of the respective diaper side margin and being positioned sufficiently closely to the batt as well as having a modulus of elasticity which is sufficient to cause the elastic member, when in a relaxed state, to longitudinally constringe the adjacent margin of the batt thereby gathering at least a portion of the respective diaper side margin, while maintaining the central portion of said outer webs and said batt generally smooth and ungathered.

12. A disposable diaper comprising: a first outer layer in the form of a moisture impervious backing; an absorbent batt positioned in superposed relationship with respect to said backing, said batt being smaller than said backing and spaced inwardly from the sides and ends thereof; a second outer layer in the form of a moisture pervious facing positioned in superposed relationship with respect to said batt, said facing being larger than said batt and having marginal portions thereof secured to said backing; an elastic member in each side margin of the diaper; means securing each elastic member to at least one of said outer layers in a condition where the elastic members are effective to foreshorten the side margins of the diaper when the elastic members are relaxed; each elastic member being positioned sufficiently closely to one side of the batt, and each elastic member having a modulus of elasticity which is sufficient to permit the elastic members to convolute the sides of the batt, in addition to gathering the sides of the outer layers adjacent thereto, when said elastic members are relaxed, while maintaining the central portion of said outer layers and said batt generally smooth and ungathered.

13. The disposable diaper in accordance with claim 12 wherein said absorbent batt is rectangularly shaped, said elastic members each being parallel to one side edge of the absorbent batt.

14. The disposable diaper in accordance with claim 13 wherein said first and second layers are rectangular and generally coterminous with one another.

15. The disposable diaper in accordance with claim 13 wherein said first and second outer layers are hourglass shaped and generally coterminous with one another.

16. The disposable diaper in accordance with claim 12 wherein a recess is provided at each side of the batt to form outwardly extending ears at each batt corner, said elastic members being located within said recesses.

17. The disposable diaper in accordance with claim 12 wherein the end portions of said batt are wider than the mid-portion thereof.

18. The disposable diaper in accordance with claim 17 wherein the sides of said batt taper outwardly from said mid-portions to said end portions.

19. The disposable diaper in accordance with claim 18 wherein the sides of said outer layers are generally parallel with the sides of said batt.

20. The disposable diaper in accordance with claim 19 wherein each elastic member is parallel with and adjacent to one side of the batt.

21. The disposable diaper of claim 17 wherein the narrowest portion of the mid-portion of the batt is offset toward one end of the diaper.

22. The disposable diaper in accordance with claim 12 wherein the height of the convolutions at the sides of the batt tapers generally uniformly from the side edges of the batt to the central region thereof.

23. A disposable diaper wherein the absorptive materials effect at least in part the gasketing around the legs of the wearer comprising: a first outer layer in the form of a moisture impervious backing; an absorbent batt positioned in superposed relationship with respect to said backing, said batt being smaller than said backing and spaced inwardly from the sides and ends thereof; a second outer layer in the form of a moisture pervious facing positioned in superposed relationship with respect to said batt, said facing being larger than said batt and having marginal portions thereof secured to said backing; and constringent means in each side margin of the diaper for reducing the length of the side margins of the diaper; said constringent means cooperating with said outer layers and said batt to bulge the side margins of the batt, in addition to gathering the side margins of the outer layers adjacent thereto, the central portion of said outer layers and said batt being generally smooth and ungathered.

*24. A disposable diaper comprising: a first outer layer in the form of a moisture-impervious backing; an absorbent batt positioned in superposed relationship with respect to said backing, said batt being smaller than said backing and spaced inwardly from the sides and ends thereof; a second outer layer in the form of a moisture-pervious facing positioned in superposed relationship with respect to said batt, said facing being larger than said batt and being substantially coterminous with said backing; side margins and end margins provided by the space between the edge of said batt and the edge of said diaper; an elastic member in each side margin of the diaper; means securing each elastic member to at least one of said outer layers to effect gathering in the side margins of the diaper when the elastic members are relaxed; and gasketing means provided by each elastic member being positioned sufficiently close to one side of the batt to at least in part effect gasketing action by the side of the batt and to produce controlled pillows at the side of the batt while the central region of the outer layers and the batt remains generally smooth and ungathered thus forming a bowl-like configuration, said pillows consisting of bulges formed in said moisture-pervious facing by the interaction of said elastic member with said moisture-impervious backing and with said moisture-pervious facing, each elastic member being at least about ¼ inch in width and having a recovery force sufficient to overcome the resistance to deformation offered by the absorbent batt.*

*25. The disposable diaper in accordance with claim 24 wherein said elastic member is an elastic ribbon of thermoplastic material.*

*26. The disposable diaper in accordance with claim 24 wherein said elastic member is an elastic ribbon at least about ½ inch wide and having a width-to-thickness ratio of at least about 100.*

*27. The disposable diaper in accordance with claim 24 wherein said absorbent batt is rectangularly shaped and said elastic members each being parallel to the side edge of the absorbent batt.*

*28. The disposable diaper in accordance with claim 27 wherein said first and second outer layers are rectangular and generally coterminous with one another.*

*29. The disposable diaper in accordance with claim 27 wherein said first and second outer layers are hourglass shaped and generally coterminous with one another.*

*30. The disposable diaper in accordance with claim 24 wherein a recess is provided at each side of the batt to form outwardly extending ears at each batt corner, said elastic members being located within said recesses.*

*31. A disposable diaper comprising: a first outer layer in the form of a moisture impervious backing; an absorbent batt positioned in superposed relationship with respect to said backing, said batt being smaller than said backing and spaced inwardly from the sides and ends thereof; a second outer layer in the form of a moisture pervious facing positioned in superposed relationship with respect to said batt, said facing being larger than said batt and having marginal portions thereof secured to said backing; an elastic member in each side margin of the diaper for reducing the length of the side margins of the diaper; said elastic members being attached to at least one of said outer layers and cooperating with said outer layers and said batt to bulge the side margins of the batt, in addition to gathering the side margins of the outer layers adjacent thereto, the central portion of said batt being generally smooth and ungathered.*

*32. The disposable diaper in accordance with claim 31 in which each said elastic member is secured along at least a portion of its length to said first outer layer.*

*33. The disposable diaper in accordance with claim 31 in which a recess is provided at each side of the batt to form outwardly extending ears at each batt corner, in which a portion of the length of each said elastic member is located along a side of said batt at said recess, and in which each ear of said batt overlaps a portion of the length of one of said elastic members.*

*34. The disposable diaper in accordance with claim 31 in which a central portion of said first outer layer is generally smooth and ungathered.*

* * * * *